United States Patent
Rogan et al.

(10) Patent No.: US 11,944,127 B2
(45) Date of Patent: Apr. 2, 2024

(54) VAPOUR GENERATING DEVICE

(71) Applicant: JT International S.A., Geneva (CH)

(72) Inventors: Andrew Robert John Rogan, Forres (GB); Damian Dickson, Ballymena (GB)

(73) Assignee: JT International S.A. (CH)

( * ) Notice: Subject to any disclaimer, the term of this patent is extended or adjusted under 35 U.S.C. 154(b) by 513 days.

(21) Appl. No.: 17/293,174

(22) PCT Filed: Dec. 18, 2019

(86) PCT No.: PCT/EP2019/085976
§ 371 (c)(1),
(2) Date: May 12, 2021

(87) PCT Pub. No.: WO2020/127501
PCT Pub. Date: Jun. 25, 2020

(65) Prior Publication Data
US 2022/0007735 A1    Jan. 13, 2022

(30) Foreign Application Priority Data
Dec. 20, 2018  (EP) ..................................... 18214880

(51) Int. Cl.
*A24F 40/53* (2020.01)
*A24F 40/20* (2020.01)
*A24F 40/485* (2020.01)
*A24F 40/51* (2020.01)
*A24F 40/57* (2020.01)

(52) U.S. Cl.
CPC .............. *A24F 40/53* (2020.01); *A24F 40/20* (2020.01); *A24F 40/485* (2020.01); *A24F 40/51* (2020.01); *A24F 40/57* (2020.01)

(58) Field of Classification Search
CPC ............................... A24F 40/53; A24F 40/485
See application file for complete search history.

(56) References Cited

U.S. PATENT DOCUMENTS

| 2014/0096781 A1* | 4/2014 | Sears ...................... A24F 40/50 131/328 |
| 2018/0168223 A1 | 6/2018 | Zinovik et al. |

(Continued)

FOREIGN PATENT DOCUMENTS

| WO | 2013098396 A2 | 7/2013 |
| WO | 2016062786 A1 | 4/2016 |

(Continued)

OTHER PUBLICATIONS

International Search Report for Application No. PCT/EP2019/085976, dated Feb. 12, 2020, 5 pages.

*Primary Examiner* — Neil Abrams
(74) *Attorney, Agent, or Firm* — Lerner David LLP

(57) ABSTRACT

A vapour generating device includes an oven arranged to receive a substrate to be vapourized, an inlet, an outlet, an airflow passageway for providing a fluid connection between the inlet and the outlet via the oven through which generated vapour can flow from the oven to the outlet. A device controller and a humidity sensor for generating a measurement of a vapour produced by the substrate are provided. The controller is operable to control the operation of the device based on measurement data from the humidity sensor.

11 Claims, 3 Drawing Sheets

(56) References Cited

U.S. PATENT DOCUMENTS

| | | | |
|---|---|---|---|
| 2018/0199630 A1 | 7/2018 | Qiu | |
| 2018/0263289 A1 | 9/2018 | Qiu | |
| 2018/0310629 A1 | 11/2018 | Qiu | |
| 2022/0151300 A1* | 5/2022 | Davidson | A24F 40/57 |
| 2023/0065955 A1* | 3/2023 | Kim | A24F 40/53 |

FOREIGN PATENT DOCUMENTS

| | | |
|---|---|---|
| WO | 2016135271 A1 | 9/2016 |
| WO | 2017207442 A1 | 12/2017 |
| WO | 2018007937 A2 | 1/2018 |
| WO | 2018019533 A1 | 2/2018 |

* cited by examiner

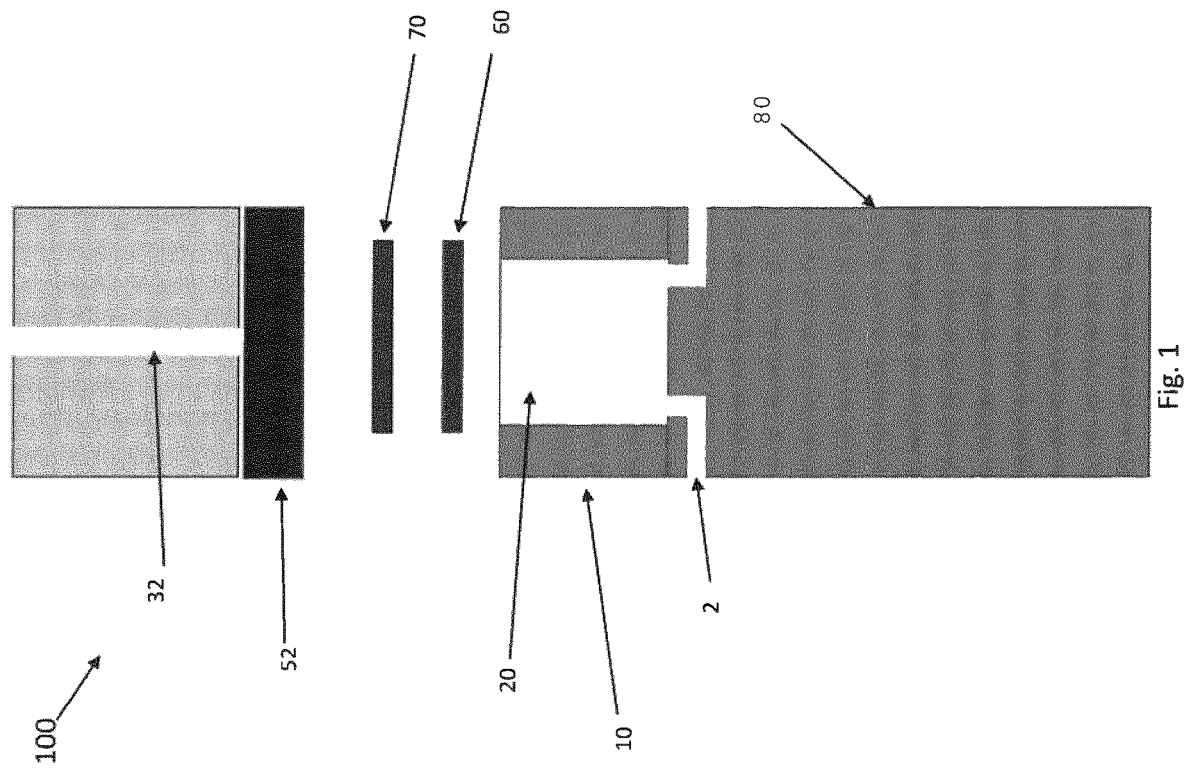

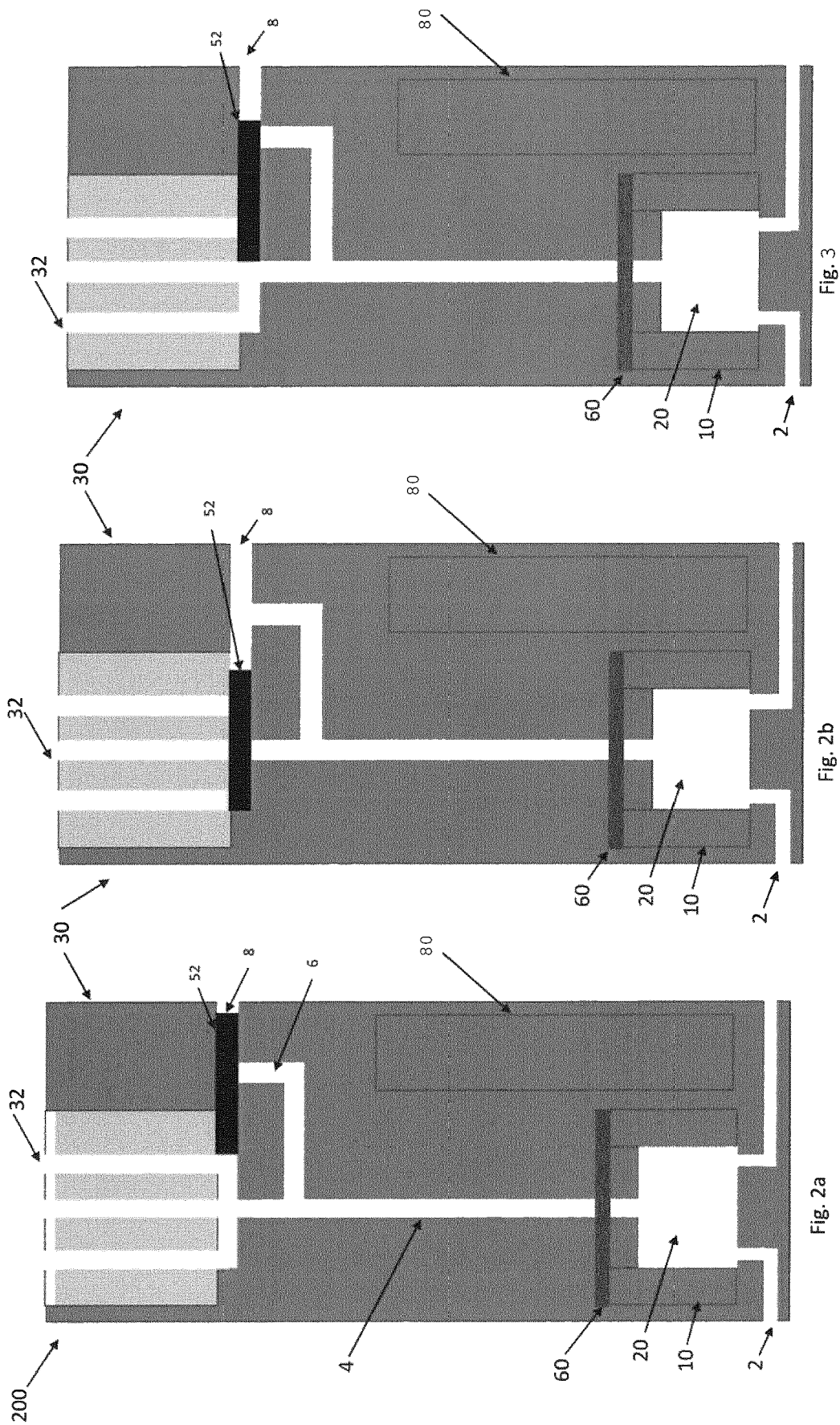

VAPOUR GENERATING DEVICE

CROSS-REFERENCE TO RELATED APPLICATIONS

The present application is a national phase entry under 35 U.S.C. § 371 of International Application No. PCT/EP2019/085976, filed Dec. 18, 2019, published in English, which claims priority to European Application No. 18214880.9 filed Dec. 20, 2018, the disclosures of which are incorporated herein by reference.

TECHNICAL FIELD

The present invention relates to a vapour generating device with control features.

TECHNICAL BACKGROUND

Devices which heat, rather than burn, a substance to produce a vapour for inhalation have become popular in recent years.

Many hand-held vapour generating devices comprise a chamber surrounded by a heating mechanism and connected to a mouthpiece. A vapour-generating substance is placed inside the chamber and the heating mechanism causes a vapour to be generated, which can be inhaled by the user through the mouthpiece.

Many hand-held vapour generating devices are arranged to receive solid vapour generating material inserted therein by the user. Therefore, it can happen that a non-genuine or otherwise unsuitable vapour-generating substance is placed inside the vaporizing chamber.

It is therefore desirable to mitigate against the risks associated with the use of non-genuine or fake or otherwise unsuitable substrate in vapour generating devices.

A further object of the present invention is to minimise exposure of the user to adverse/undesirable components that could be present in the generated vapor from the vapour generating device.

Another object of the present invention is to regulate the resistance to draw of a user using a vapour generating device.

SUMMARY OF THE DISCLOSURE

According to the present invention, there is provided a hand-held vapour generating device for producing a vapour for inhalation by a user, this device comprising: an oven arranged to receive a vapour generating substrate; an inlet; an outlet; an airflow passageway for providing a fluid connection between the inlet and the outlet via the oven and through which generated vapour can flow to the outlet; a device controller; a humidity sensor for generating a measurement of a vapor produced by said substrate, wherein the device controller is arranged to control the operation of the device based on measurement data from the humidity sensor; and a gas sensor for measuring adverse/undesirable components in the produced vapor, such that when the device controller determines that a substrate is genuine, based on the measurement data from the humidity sensor, said gas sensor takes measurement of the generated vapor.

The present invention enables the control of the operation of the device to be dependent upon the properties of the vapour produced by the device as determined by the humidity sensor. For example, if the humidity sensor generates a measurement of the vapour which is outside of an expected range, the operation of the device can be stopped to minimise the amount of potentially inappropriate vapour inhaled by the user.

Different humidity sensors are available which operate differently and may be affected differently by the vapour; however, all that is required for the present invention is that the humidity sensor is affected by the vapour and generates a consistent measurement when measuring the vapour produced by the device from similar substrates. In this way the actual output from the humidity sensor can be compared with predetermined expected output from the sensor in order to detect that the generated vapour is potentially inappropriate.

The oven can be heated in a number of different ways. Typically, for example the oven will be (at least partially) surrounded by an electrical resistance heating mechanism. There may be however some other heating mechanism such as an induction coil for directly heating the oven if it is formed out of a suitable material which is susceptible of being heated when subjected to an alternating magnetic field generated by the induction coil, for example.

In one embodiment, control of the device is dependent upon the data from the humidity sensor simply comprises switching off the heater of the oven if the data from the humidity sensor is determined by the controller as being outside of a predetermined range of acceptable values from the humidity sensor. This provides a simple way of minimising the amount of potentially inappropriate vapour inhaled by the user.

The device may further include an automatic flow control mechanism, which comprises a flow control element positioned between said oven and said outlet, and an actuator for actuating the flow control element. This can adjust the flow of vapour or air, etc. around or through the flow control element, for example the actuator can cause the flow control element to change its position or orientation or to cause a flow constricting aperture, e.g. a valve, to adjust its diameter, etc. as described in greater detail below. In this way the automatic flow control mechanism is operable to cause the actuator to adjust the flow control element based on the humidity data from the humidity sensor under the control of the controller.

The technical effect of this is that generated vapour can be controlled (e.g. blocked or deviated away from the outlet) before reaching the outlet. This can help to reduce the amount of inappropriate vapour inhaled by the user (i.e. by quickly responding to detection of inappropriate vapour by blocking or deviating it away from the outlet before vapour reaches the user).

In this arrangement, the humidity sensor is preferably located upstream of said flow control element. By "upstream of the flow control element", it is meant that vapour generated by the substrate will generally reach the humidity sensor before it reaches the flow control element in normal use.

The device controller may be further operable to automatically deactivate said oven and/or cause the actuator to close said flow control element to prevent generated vapour from being inhaled by a user in use if the data from the humidity sensor is determined to be outside of a predetermined acceptable range.

In this way the humidity of the vapour can be detected and used to identify if an inappropriate substrate was used. This can, for example, help to determine if the inserted substrate is genuine or fake. This can help to minimise the chances of an end user inhaling inappropriate vapour.

The vapour generating device may further comprise a pressure sensor, wherein said automatic flow control mechanism is operable to cause the actuator to adjust the flow control element based on humidity data from the humidity sensor and pressure data from the pressure sensor.

In some embodiments the pressure sensor may be a simple puff sensor as commonly used in conventional e-cigarettes.

The pressure sensor enables the device to detect when a user is drawing on the device and this can assist the device in determining what humidity data to take into account (e.g. the device can wait until the pressure sensor detects an increased pressure indicative of a user taking a draw and can then request the humidity sensor to take humidity readings based on such a trigger). This can improve the effectiveness of the operation of the device. This also help to saves energy consumption of the device by not continuously interrogating the humidity sensor.

In other embodiments, the pressure sensor may be a differential-value pressure sensor capable of measuring different pressure values (rather than simply detecting if the pressure exceeds a predetermined threshold as is the case with simple puff sensors).

Where such a multi-value pressure sensor is used, because the predetermined humidity range may depend upon the pressure detected by the pressure sensor (e.g. because a different humidity range will be appropriate for a greater or lesser amount of substrate which may affect the pressure detected by the pressure sensor), the accuracy of the vapour assessment when compared to using a humidity sensor alone can be improved.

Additionally, where the vapour generating device is intended to be used with loose leaf substrates (e.g. loose tobacco) the use of a multi-value pressure sensor which is connected to an automatic flow control mechanism enables a consistent resistance to draw (RTD) to be achieved, even if different amounts of substrate are packed into the oven (affecting the resistance to draw through the oven), by having the automatic flow control mechanism compensate for such changes in RTD through the oven to achieve a substantially consistent RTD through the device as a whole.

This helps to ensure a substantially consistent resistance to draw (RTO) for different amounts or type of material into the oven, for example loosely versus more compactly packed material.

Additionally, the use of a multi-value pressure sensor connected to an automatic flow control mechanism enables the device to automatically adjust the RTD depending on the suction force of the user—e.g. a user with a large suction force may generally prefer a greater RTD compared to a user who has a lower suction force. The device can detect the suction force with the pressure sensor and thus adjust the RTD accordingly. This allows the device to provide a suitable RTD level customized to a user.

More advantageously, where the pressure sensor is operable to detect a puff on the device by a user when in use and then to provide a signal for activating said oven and said humidity sensor, the humidity sensor can measure a humidity level of the produced vapour after the user has initiated a puff.

This has the advantage of helping to ensure that the generated vapour is in the vicinity of the humidity sensor when a measurement is taken. This helps to prevent wrong measurements by the humidity sensor being taken. Thus, generally improving the reliability and/or quality of the measurement data.

Preferably, the device is further configured to enable the device controller to regulate the RTD of the device to a desirable level for the user based on the measured pressure level of a puff taken in use, only when said substrate is determined as being genuine (i.e. is not determined as being inappropriate based on the detected humidity level).

This allows to regulate the RTD to a desirable level for the user only when the substance is genuine. This also allows provision of a better user-experience.

The use of a gas sensor in conjunction with the humidity sensor can further improve the accuracy of determining if an appropriate substrate has been inserted into the device.

In one embodiment, the gas sensor is only activated to take a measurement when the substrate is not detected as being inappropriate based on the humidity data.

This allows a supplementary control of the quality of the vapour that is drawn by an end-user. This is achieved by controlling not only the authenticating of the substance held in the oven based on humidity data alone but also by controlling the cleanliness of the vapour sucked by the end-user, in terms of undesirable components, toxicity, etc. Therefore, this allows to further improve the user experience.

Preferably, the flow control mechanism is configured to close the flow control element (to minimise the amount of generated vapour inhaled by the user) when the detected gas is determined to be not acceptable based on the measurements of the gas sensor. This helps to avoid a user inhaling adverse components.

Preferably, the pressure sensor is further configured to measure a pressure level of said puff applied in said device in use, such that when the detectable gas is acceptable, based on said pressure level delivered by the pressure sensor, the processor adjusts the flow control mechanism in order to regulate the RTD.

This allows regulation of the RTD to be customized for a user only when the detected gas is acceptable. Thus, improving user-experience.

Preferably, the flow controllable element is one of: a shutter, a valve, an inlet, and a rotary hole closure mechanism.

BRIEF DESCRIPTION OF THE DRAWINGS

The invention will now be described with reference to the drawings, which by way of example illustrate embodiments of the present invention and in which like identical features present in the embodiments are assigned the same reference numerals.

FIG. 1 is a schematic exploded view of a vapour generating device 100 according to an exemplary embodiment of the invention.

FIG. 2a is a schematic view of a vapour generating device showing the flow control element in a closed position according to an exemplary embodiment of the invention.

FIG. 2b is a schematic view of a vapour generating device showing the flow control element in an opened position according to an exemplary embodiment of the invention.

FIG. 3 is a schematic view of the device 300 when the flow control element acts as a RTD regulator according to an exemplary embodiment of the present invention.

DETAILED DESCRIPTION OF EMBODIMENTS

Figure 4:
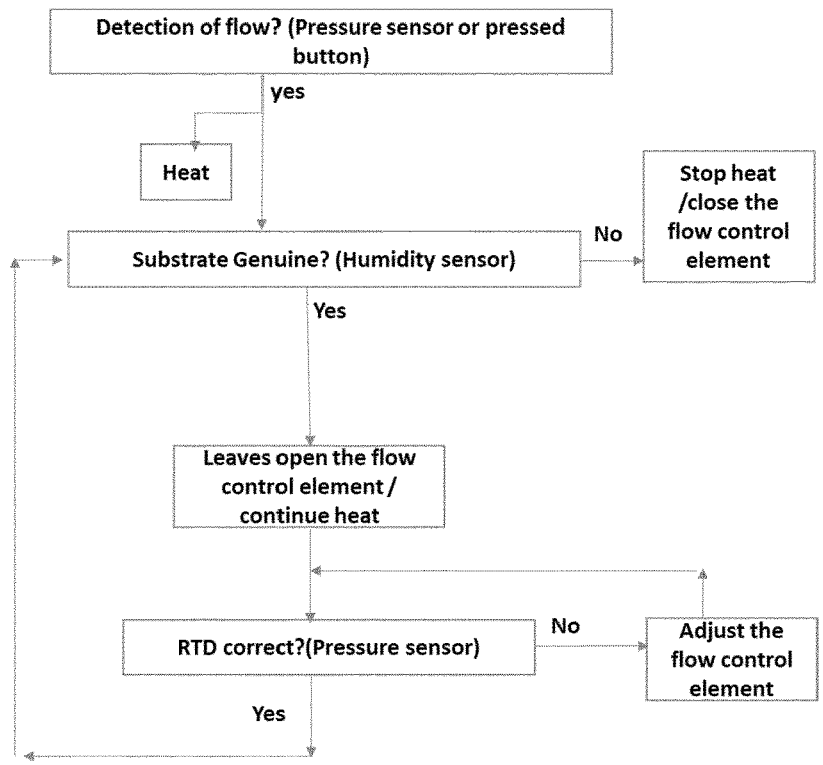
FIG. 4 and FIG. 5 are flow diagrams showing operation of the device of the invention.

FIGS. 1, 2a, 2b and 3, show vapour generating devices 100, 200 according to the present invention. Each comprises an oven 10 arranged to receive a substrate 20 comprising material to be vaporized, a mouthpiece 30 with an air outlet 32. An airflow passageway 40 provides a fluid connection between the oven 10 and the outlet 32 through which the generated vapour can flow from the oven 10 to the outlet 32 and then to the mouth of a user. The oven can be based on resistive heating technology or induction heating technology. The substrate 20 can, for example, be tobacco loose leaf or mousse, although other substrates are possible. Each device 100, 200 further comprises central electronics configured to control the operation of the devices through to device components described below.

In general terms, in use, when a user inserts or provides a substrate 20 within the oven 10, the user draws on the device 100 and activates the oven via a flow sensor (puff or pressure sensor—not shown) placed around air inlets 2 for detecting air entering when a user draws. This provides a signal to a processor (not shown) to activate the oven 10. Alternatively, the user can activate the oven 10 using a press-button (not shown) on the device 100. The produced vapour flows from the oven 10 to the outlet 32 and then to the mouth of the user who inhales the vapour.

In a first embodiment of the present invention, the device 100 further includes an automatic flow control mechanism, which comprises a flow control element 52 and an actuator. The flow control element 52 can be positioned between the oven 10 and the mouthpiece 30.

The device 100 further comprises a humidity sensor 60 for measuring humidity data of a vapor produced by the substrate 20.

The flow control mechanism operates to cause the actuator to adjust the flow control element 52 based on the humidity data from the humidity sensor 60.

The humidity sensor 60 is located upstream of the flow control mechanism. The humidity sensor 60 can alternatively be located in or in the vicinity of the airflow passageway in order to detect the generated vapour passing through the airflow passageway. It will be appreciated that humidity sensors of different types are known in the art. If the device uses a humidity sensor which is affected by the presence of aerosol droplets in the vapour, the measurement from the humidity sensor may not accurately reflect the humidity of the vapour (in terms of the amount of water vapour held in the air entrapping the aerosol droplets). In such a case the humidity level may not accurately reflect the actual humidity (e.g. the relative humidity) of the vapour in the normal sense, however such a measurement is sufficient for the purposes of the present invention and therefore we continue to use the term humidity level for either a case where the humidity sensor provides an actual humidity level or simply a value which depends upon the properties of the vapour which it is measuring.

If provided a pressure sensor is arranged to detect when a puff is taken and to provide signal to the humidity sensor 60 whereby the humidity sensor can take a measurement of the humidity level when a puff has been detected. In other words, the humidity sensor can be arranged to take a measurement based on an activation signal from the pressure sensor. This has the advantage of ensuring the vapour is in the vicinity of the humidity sensor when a measurement is taken.

The processor (of the device electronics 80) is also arranged to communicate with the oven 10 such that, based on the humidity data provided by the humidity sensor 60, the processor can automatically deactivate the oven 10 and/or cause the actuator 54 to close the flow control element 52, if the humidity data indicates that the substrate 20 is not appropriate (because it is not genuine for example). This has the advantage of preventing the generated vapour (from an inappropriate substrate) from being inhaled by a user in use. In a case where the humidity sensor is operable to measure the relative humidity of water vapour in the air (regardless of the presence of aerosol droplets), a predetermined threshold value of the humidity level above which the controller automatically deactivates the oven 10 can be between 5% to 20%, advantageously 7 to 15%, more advantageously it is around 10%.

In use, when a user inserts a substrate 20 into the oven 10, the user draws on the device 100 or presses a button, the oven 10 is activated to heat the substrate 20 using one of the alternative solutions disclosed above. The humidity sensor 60 then measures the humidity level of the generated vapour. There is usually a delay between the activation of the oven 10 and the humidity sensor 60 which can be set to be between 1 second to 2 minutes, depending on the heater technology, typical times for induction heating technology is about 1 to 5 seconds while for resistive heating technology it will be closer to 1 minute for example. Then the measured humidity level from sensor 60 is sent to the processor, and when the level is above the humidity threshold value, meaning that the substrate is not genuine, the processor stops the oven and/or closes the flow control element 52. When the humidity level is equal to or less than the predetermined threshold value, the oven is left on to continue to heat the substrate and the flow control element is left open, such that the outlet 32 of the mouthpiece is left on and the user can continue to use the device 100.

In the context of this invention, the flow control element 52 can be a shutter. There are a number of advantages for this. For example, the shutter can be used to regulate different levels of RTD, and can be used as an outlet for evacuating undesirable generated vapour for example in the case that the humidity level is above the threshold value, then the generated vapour can be expelled or evacuated from the device. Alternatively, the shutter can be an inlet for allowing ambient air in to the airflow to dilute the produced vapour. The shutter can be a simple valve. Alternatively, the shutter can be a rotary hole closure mechanism.

In the context of the present invention, the components such as the sensors 60, 70, the flow control mechanism are connected to the processor. Alternatively, each component can be embedded in a single processor component that communicates with another centralised processor.

Alternatively, the flow control mechanism can operate to cause the actuator to adjust the flow control element 52 based on the humidity data and the pressure data. In this case, the pressure sensor is operable to detect a puff on the device by a user when in use as described above, such that, when a puff is taken, the pressure sensor is operable to detect the puff, and then to provide a signal for activating the oven 10 and for activating the humidity sensor 60, such that the humidity sensor 60 measures a humidity level of the produced vapour. In other words, the humidity level of the produced vapour will be measured only when the humidity sensor 60 receives signal from the pressure sensor. This has the advantage to ensure that the vapour is in the vicinity of the humidity sensor when a measurement is taken.

In the context of the present invention, the outlet 32 can alternatively be defined as multiple outlets allowing the generated vapour to flow through the multiple outlets to the mouth of a user.

As shown in FIGS. 2a and 2b, a further device 200 according to the invention comprises multiple air outlets 32, and the mouthpiece 30 of the device 200 has multiple air outlets 32. The air outlets are connected to the vapor passageway 4, which is in fluid communication with the oven 10. Preferably there is a supplementary vapour passageway 6. This second vapour passageway 6 is arranged to be fluidly connected to the vapour passageway 4 at one end and to a second outlet 8 at another end, which opens to the exterior of the device 200. The second vapor passageway 6 is arranged such that, when the control flow element 52 is in an open position, when the substrate is genuine, the generated vapour travels through the vapour passageway 4 to the air outlets 32, the flow control element 52 blocks the second vapour passageway 6. When the flow control element 52 is in a closed position, for example, when it has been determined that the substrate is not genuine, the control flow element 52 allows vapour through the second vapour passageway 6 in a way that if the produced vapour contains adverse components, these can be expelled from the device 200 through the second outlet 8 as shown in FIGS. 2a and 2b respectively.

A further embodiment of the present invention is similar to the first embodiment except that the pressure sensor is further configured to measure a pressure level of the puff applied by the user to the device in use, such that when the substrate 20 is genuine, based on the pressure level, the processor adjusts the flow control mechanism in order to regulate the RTD. This has the advantage to provide a tailor-made RTD adapted to each user's needs.

The flow of operation for this is schematically described in the flowchart of FIG. 4.

Referring now to FIG. 3, the flow control element 52 can be arranged to move partially, in other words the flow control element 52 can be arranged to be partially open such that the flow control element 52 still closes the second vapour passageway 6 while leaving only some or part of the air outlets 32 open, such that the generated vapour can still reach the mouth of the user. In this way, the flow control element acts as an RTD regulator. The number or portion of air outlets left open is a function of the pressure level measured by the pressure sensor, thus this number is a function of the draw strength of each specific user.

Alternatively, the flow control element 52 can act as a diluent element for example by leaving open the outlet 8. This allows air entering the device and through the vapour passageway 4 to contribute to dilute the vapour. This also allows a decrease in the temperature of the produced vapour before it goes into the mouth of a user.

According to another embodiment, the vapour generating device 100 is similar to earlier embodiments except that the vapour generating device 100 or 200 further comprises a gas sensor 70 for measuring potential adverse/undesirable components in the produced vapour. When the substrate is genuine, based on the humidity data, the gas sensor 70 takes a measurement of the generated vapor as well as the humidity sensor. This further measurement of the generated vapour is performed by the gas sensor 70 only when the substrate is not detected as being inappropriate by the humidity sensor 60 and allows a further measurement of the vapor generated that can be further used to prevent a user from inhaling adverse components.

In this example the flow control element is also configured to close the outlet 32 when the detected gas is determined to be not acceptable based on the measurements of the gas sensor. Again, this has the advantage to prevent a user to inhale adverse components in case the gas sensor level value is above a gas sensor threshold value. The threshold value in this case can be between 1 to 10% presence of a gas or toxic entity or substance. A toxic entity can be chemical, biological or physical. An example chemical can be carbon dioxide or carbon monoxide. Different types of gas sensors can be used depending on the purpose for which the gas sensor is to be used or depending upon the substance (s) to be detected. For example, the gas sensor can be a flame ionization detector, semiconductor, electrochemical or photonic membrane sensor.

Figure 5:
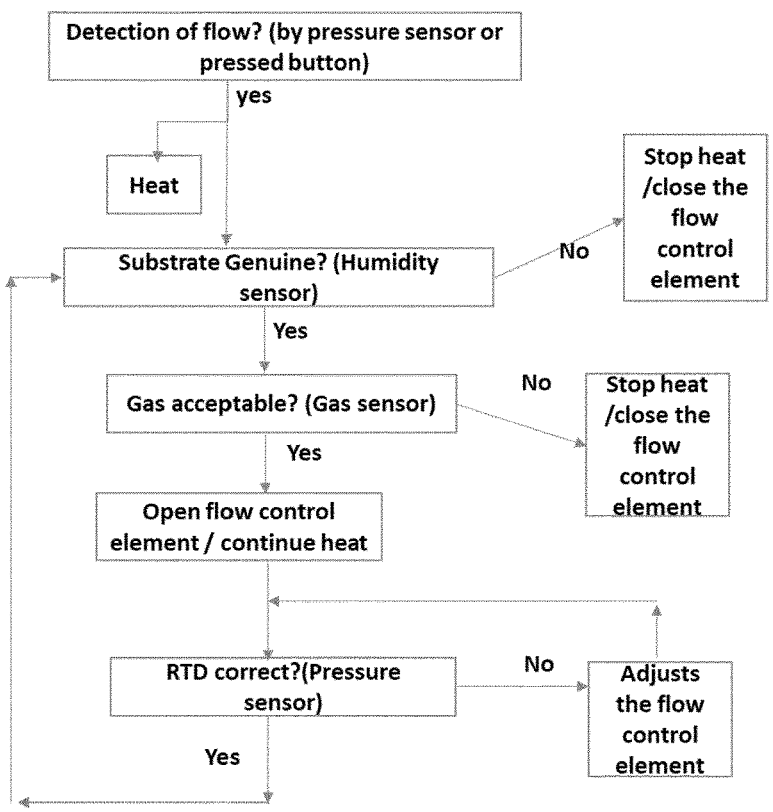

Again, based on the pressure level of a puff applied in the device 100 by the user, as determined by the pressure sensor, for example in the situation where the detectable gas is acceptable, the processor can adjust the flow control element based on the pressure level, to regulate the RTD. Preferably, the processor adjusts the flow control element 52, and/or the processor adjusts the actuator. The entire flow is schematically described in the flowchart of FIG. 5.

It will be appreciated the gas sensor of this example can be employed with the device of any of the other examples.

REFERENCE NUMBERS USED FOR THE FIGURES

| | |
|---|---|
| 100/200 | Vapour generating device |
| 2 | Air inlets |
| 4 | Vapour passageway |
| 6 | Second vapor passageway |
| 10 | Oven |
| 20 | Substrate |
| 30 | Mouthpiece |
| 32 | Air outlet |
| 8 | Second outlet |
| 52 | Flow control element |
| 60 | Humidity sensor |
| 70 | Gas sensor |

The invention claimed is:

1. A hand-held vapour generating device for producing a vapour for inhalation by a user, the device comprising:
   an oven arranged to receive a vapour generating substrate;
   an inlet;
   an outlet;
   an airflow passageway for providing a fluid connection between the inlet and the outlet via the oven and through which generated vapour can flow to the outlet;
   a device controller;
   a humidity sensor for generating a measurement of a vapour produced by said substrate, wherein the device controller is arranged to control operation of the device based on measurement data from the humidity sensor; and
   a gas sensor for measuring adverse/undesirable components in the produced vapour, such that when the device controller determines that a substrate is genuine, based on the measurement data from the humidity sensor, said gas sensor takes measurement of the generated vapour.

2. The vapour generating device according to claim 1, wherein the device controller is arranged to control the device in dependence upon the data from the humidity sensor, and switches the oven off if the data from the humidity sensor is determined by the device controller as being outside of a predetermined range of acceptable values from the humidity sensor.

3. The vapour generating device according to claim 1, further comprising an automatic flow control mechanism comprising a flow control element positioned between the oven and the outlet, and an actuator for actuating the flow control element, wherein, the automatic flow control mechanism is arranged to cause the actuator to adjust the flow control element based on the measurement data from the humidity sensor under the control of the device controller.

4. The vapour generating device according to claim 3, further comprising a pressure sensor, wherein said automatic flow control mechanism is arranged to cause the actuator to adjust the flow control element based on measurement data from the humidity sensor and pressure data from the pressure sensor.

5. The vapour generating device according to claim 4, wherein the pressure sensor is a multi-value pressure sensor arranged to measure different pressure values.

6. The vapour generating device according to claim 4, wherein the pressure sensor is arranged to detect a puff on the device by a user in use, such that, when a puff is taken, the pressure sensor detects the puff and provides a signal for activating the oven and the humidity sensor.

7. The vapour generating device according to claim 4, wherein the pressure sensor is further configured to measure a pressure level of a puff applied to the device in use, such that when the device controller determines that the substrate is genuine, based on the measurement data from the humidity sensor, based on said pressure level, said actuator adjusts said flow control element in order to regulate a resistance to draw (RTD).

8. The vapour generating device according to claim 3, wherein the humidity sensor is located upstream of said automatic flow control mechanism and in, or in the vicinity of, the airflow passageway in order to detect vapour passing through the airflow passageway.

9. The vapour generating device according to claim 3, wherein the device controller is further arranged to automatically deactivate the oven and/or cause the actuator to close the flow control element to prevent generated vapour from being inhaled by a user in use if the detected humidity of the generated vapour is determined to be outside of a pre-determined acceptable range.

10. The vapour generating device according to claim 3, wherein said automatic flow control mechanism is arranged to close when a detected gas is determined to be not acceptable based on the measurements of the gas sensor.

11. The vapour generating device according to claim 3, wherein the flow control element is one of: a shutter, a valve, an inlet, and a rotary hole closure mechanism.

* * * * *